United States Patent
Bekker et al.

(10) Patent No.: US 9,918,946 B2
(45) Date of Patent: Mar. 20, 2018

(54) PETROLATUM COMPOSITION

(71) Applicant: Sasol Chemical Industries Limited, Johannesburg (ZA)

(72) Inventors: Madelyn Bekker, Sasolburg (ZA); Glenda Vanessa Webber, Vanderbijlpark (ZA); Corina Jacobs, Vereeniging (ZA); Nicolaas Russouw Louw, Vanderbijlpark (ZA); Noël Thomas Montgomery, Amanzimtoti (ZA); Vernon Johan Jansen Van Rensburg, Vanderbijlpark (ZA)

(73) Assignee: Sasol Chemical Industries Limited, Johannesburg, Gauteng Province (ZA)

( * ) Notice: Subject to any disclaimer, the term of this patent is extended or adjusted under 35 U.S.C. 154(b) by 119 days.

(21) Appl. No.: 14/361,204

(22) PCT Filed: Nov. 28, 2012

(86) PCT No.: PCT/IB2012/056793
§ 371 (c)(1),
(2) Date: May 28, 2014

(87) PCT Pub. No.: WO2013/080138
PCT Pub. Date: Jun. 6, 2013

(65) Prior Publication Data
US 2014/0336272 A1 Nov. 13, 2014

(30) Foreign Application Priority Data

Nov. 29, 2011 (ZA) .................. 2011/08766

(51) Int. Cl.
C07C 2/66 (2006.01)
A61K 31/01 (2006.01)
A61K 8/31 (2006.01)
A61Q 19/00 (2006.01)
C08L 91/06 (2006.01)

(52) U.S. Cl.
CPC .............. *A61K 31/01* (2013.01); *A61K 8/31* (2013.01); *A61Q 19/00* (2013.01); *C08L 91/06* (2013.01)

(58) Field of Classification Search
None
See application file for complete search history.

(56) References Cited

U.S. PATENT DOCUMENTS

| 1,791,926 | A | 2/1931 | Gallagher |
| 2,828,248 | A | 3/1958 | Leonard |
| 7,851,663 | B2 | 12/2010 | Abhari |
| 7,875,166 | B2 | 1/2011 | Matthai et al. |
| 2004/0167368 | A1* | 8/2004 | Michel Fenouil ..... C10G 45/00 585/323 |
| 2004/0192979 | A1 | 9/2004 | Matthai et al. |

FOREIGN PATENT DOCUMENTS

| CN | 101892080 A | 11/2010 |
| GB | 955348 A | 4/1964 |
| JP | 2009-234991 A | 10/2009 |

OTHER PUBLICATIONS

Colloids and Surfaces, Physicochemical and Engineering Aspects, vol. 152, 1999, pp. 89-94.
T. K. Parkins; J.B. Turner: 'Starting Behavior of Gathering Lines and Pipelines Filled with Gelled Prudhoe Bay' J.Pet. Technol vol. 23, 1971, pp. 301-308.
International Search Report, International Patent Application No. PCT/IB2012/056793, dated Feb. 10, 2013, 4 pages.
Colloids and Surfaces, Physicochemical and Engineering Aspects vol. 152, 1999, pp. 89-94.
M. Bekker et al: "The benefits of Fischer-Tropsch waxes in synthetic petroleum jelly", International Journal of Cosmetic Science, vol. 35, No. 1, Feb. 27, 2013 (Feb. 27, 2013), pp. 99-104, XP055076224, ISSN: 0142-5463, DOI: 10.1111/ics.12011.
S. M. Battarjee et al: "Preparation of Medicinal Petroleum Jelly using Local Petroleum Waxes", Lubrication Science, No. 12, Nov. 1, 1989 (Nov. 1, 1989), XP055078014, ISSN: 0954-0075.
T. K. Parkins; J.B. Turner: 'Starting Behavior of Gathering Lines and Pipelines Filled with Gelled Prudhoe Bay' J. Pet. Technol vol. 23, 1971, pp. 301-308.

* cited by examiner

*Primary Examiner* — Hasan Ahmed
(74) *Attorney, Agent, or Firm* — Fitch, Even, Tabin & Flannery, LLP

(57) ABSTRACT

A petrolatum composition comprises from 10 to 60 wt % of a wax having an average number of carbon atoms per molecule of between 25 and 70, and having between 5 and 50 wt % branched paraffins in which the branches are selected from methyl and ethyl branches; from 10 to 60 wt % of a linear paraffin having an average number of carbon atoms per molecule of between 10 and 20; and optionally, a low melt wax. The petrolatum composition has a drop melt point of from 35° C. to 80° C.

14 Claims, 2 Drawing Sheets

PETROLATUM COMPOSITION

CROSS REFERENCE TO RELATED APPLICATIONS

Figure 1:
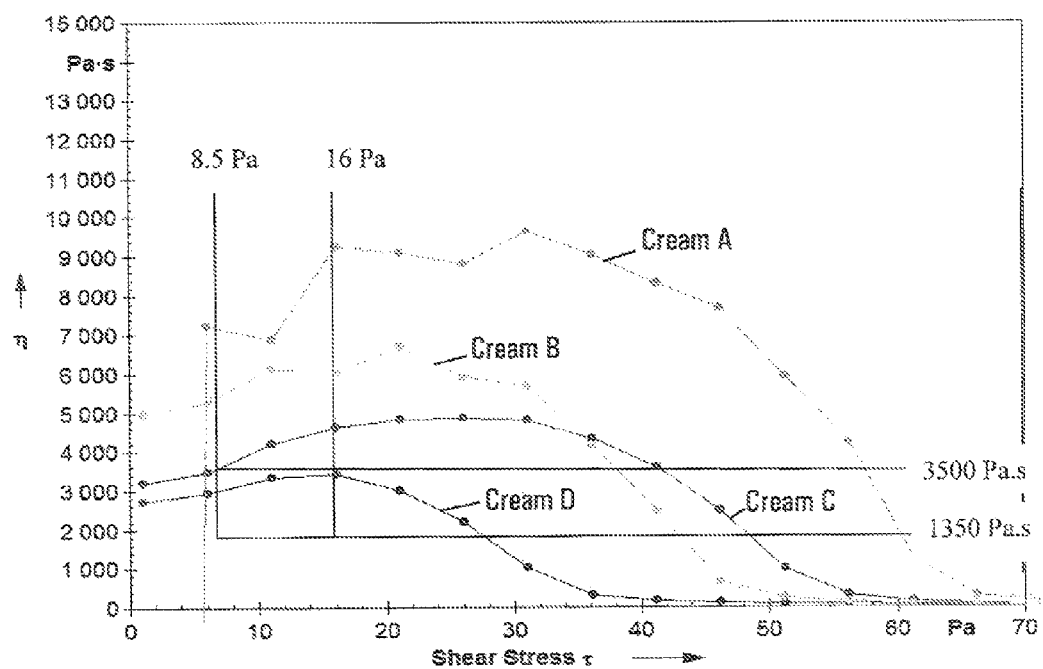

This application is a national phase application of International Application No. PCT/IB2012/056793, filed Nov. 28, 2012, designating the United States and claiming priority to South African Patent Application No. 2011/08766, filed Nov. 29, 2011, both of which are incorporated by reference as if fully rewritten herein.

BACKGROUND

THIS INVENTION relates to a petrolatum composition.

Petrolatum (petroleum jelly) is a soft, oily, semi-solid mixture of hydrocarbons obtained from high-boiling hydrocarbons and hydrocarbons which are normally liquid at room temperature. Depending on their purity, petrolatums range in colour from dark petrolatum which is impure to highly pure petrolatum which is normally white in colour.

Typical properties of a petrolatum are that it should be a soft unctuous mass and be slightly fluorescent in daylight when molten. A petroleum jelly should be practically insoluble in water, soluble in methylene chloride or hexane, and practically insoluble in alcohol and in glycerol.

Petroleum jellies have a wide range of applications such as pharmaceutical ointment bases, infant care, cosmetics, leather care, elastomers and as a grease or lubricant. Petroleum jelly products are used for human consumption and should therefore be of high purity. For example, the product should contain less than 1 ppm polycyclic aromatic hydrocarbons (which are carcinogenic) and the petroleum jelly should pass acidity/alkalinity and sulphated ash tests.

A white petroleum jelly/petrolatum is a purified and wholly or nearly decolourised mixture of semi-solid hydrocarbons ($C_nH_{2n+2}$), obtained from petroleum and high-boiling liquid hydrocarbons. It should have a white, or almost white, translucent appearance.

Petrolatums are conventionally produced by blending petroleum derived oil components with slack waxes. Slack waxes are obtained during a de-waxing process of lubricant base-oils from crude oil. Such petroleum based petrolatums are described in U.S. Pat. Nos. 2,828,248 and 1,791,926. Although the term 'petrolatum' originates from petroleum, which is a fossil fuel derived product, petrolatum also includes those types which are derived from synthetic sources, being those of which the molecules of at least one component (or all of its components) were derived by chemical synthesis. Petrolatum may also contain natural components such as vegetable waxes.

GB 955348 suggests a blend of 10-30% of Fischer-Tropsch wax with 35-45% petroleum and 35-45% of liquid polypropylene, for use as a cable impregnant. JP 2009-234991 describes the use of a Fischer-Tropsch wax and a liquid paraffin to provide a stick cosmetic. The properties of a stick cosmetic are however very different to that of a petrolatum in that a stick cosmetic is not an unctuous paste, which a petrolatum is. Instead, a stick cosmetic is more solid and harder than a petrolatum because it needs mould release properties.

The use of synthetic components in petrolatum has been suggested in U.S. Pat. Nos. 7,851,663, 3,764 and JP 2009-234991. U.S. Pat. No. 7,851,663 teaches the grafting of long chain olefins and paraffins produced by Fischer Tropsch synthesis, to yield iso-paraffins with long-chain branching exhibiting properties of petrolatum.

Synthetic waxes, eg. those obtained from the Fischer-Tropsch process, do not contain significant amounts of aromatic and polynuclear aromatic components, which is beneficial for petrolatum. However, when synthetic components are used in a petrolatum formulation, obtaining the desired stability and three-dimensional network structure of the petrolatum remains a challenge. In particular, when a petrolatum composition contains a linear paraffin which is liquid at room temperature, the linear paraffin tends to separate from the heavier components in the formulation leading to a non-stable petrolatum formulation. In order to obtain a stable composition a "solvent binding" effect is required.

It is an object of this invention to provide a stable petrolatum containing normally liquid linear paraffins.

SUMMARY OF THE INVENTION

According to a first aspect of the invention, there is provided a petrolatum composition comprising from 10 to 60 wt % of a wax having an average number of carbon atoms per molecule of between 25 and 70, and having between 5 and 50 wt % branched paraffins in which the branches are selected from methyl and ethyl branches;

from 10 to 60 wt % of a linear paraffin having an average number of carbon atoms per molecule of between 10 and 20; and optionally, a low melt wax;

with the petrolatum composition having a drop melt point of from 35° C. to 80° C.

The wax (hereinafter also referred to as 'the wax component') may be an aliphatic wax. More particularly, it may be a hydrocarbon wax, and preferably it is a paraffin wax. The wax may be a synthetic wax. Preferably the wax is a macrocrystalline synthetic wax. The wax may make from 20 to 40 wt %, or even from 25% to 35% of the petrolatum composition. The wax may have an average number of carbon atoms per molecule of between 28 and 60.

The wax may have between 10 and 50 wt %, preferably between 20 and 40 wt % branched paraffins. In one embodiment of the invention, the wax has less than 25 wt % branched paraffins. Preferably the wax has a drop melt point of from 60° C. to 110° C. The wax may have between 25 and 70, preferably between 28 and 60, carbon atoms per molecule.

The wax may be selected from the group consisting of a hydroisomerised wax, a hydroisomerised Fischer-Tropsch wax, an alpha-olefin wax and a Fischer-Tropsch wax.

The linear paraffin (hereinafter also referred to as 'the linear paraffin component') may be a synthetic paraffin, and it may be a Fischer-Tropsch derived paraffin. The linear paraffin may make up from 20 to 40 wt %, or even from 25% to 35% of the petrolatum composition. Preferably the linear paraffin has a melting point below 25° C. The linear paraffin may have between 10 and 20 carbon atoms per molecule.

As used in this specification, the term "linear paraffin" means molecules having a straight-chain carbon backbone without any branches thereon (n-paraffin) and containing only carbon and hydrogen atoms. Although the source of linear paraffin used to prepare the petrolatum composition may include some branched molecules, as shown hereunder in Table 1 under the heading "Linear Paraffin", these branched molecules are not material to the invention.

The composition may also include the low melt wax (hereinafter also referred to as 'the low melt wax component'). When the low melt wax is present, it may be a wax having a drop melt point of from 20° C. to 30° C. Preferably the low melt wax has an average number of carbon atoms per molecule of between 20 and 30. The low melt wax may have between 20 and 30 carbon atoms per molecule. The petrolatum composition may comprise from 10 to 60 wt % of the low melt wax.

The low melt wax may have between 15 and 30 wt % branched paraffins, preferably between 20 and 28 wt %. The low melt wax may be a hydrocarbon wax and preferably it is a paraffin wax. The low melt wax may be a synthetic wax and preferably it is a Fischer-Tropsch wax. The low melt wax may make up from 20 to 40 wt %, or even from 25 to 35% of the petrolatum composition.

The petrolatum composition may have a drop melt point of from 35-70° C. Preferably the petrolatum has a cone penetration (as measured by ASTM D937-07, employing the cone defined in ASTM D217-10) of between 60 and 300 mm/10.

The petrolatum may be a white unctuous paste, being slightly fluorescent in daylight when molten.

In another preferred embodiment, there is provided a petrolatum composition as described herein, wherein each of the wax component and the linear paraffin component are synthetic. In yet another preferred embodiment, each of the wax component, the linear paraffin component and the low melt wax component are synthetic components.

The applicant has surprisingly found that a stable petrolatum can be obtained with the composition disclosed herein.

According to a second aspect of this invention, there is provided the use of the petrolatum composition according to the first aspect of the invention, in a cosmetic application, a pharmaceutical application or a cable filling application. Due to the absence of aromatic components, sulphur and other skin irritants, the petrolatum is particularly suitable for use in skin care applications.

According to a third aspect of the invention, there is provided the use of the petrolatum composition according to the first aspect of the invention in the manufacture of a cosmetic product, a pharmaceutical product, a cable-filling product, or a filled cable product.

According to a fourth aspect of the invention, there is provided a method of making a cosmetic product, a pharmaceutical product, a cable-filling product or a filled cable product which includes adding the petrolatum composition according to the first aspect of the invention, to a cosmetic composition or substance, to a pharmaceutical composition or substance, to a cable-filling composition or substance, or to a cable or cable component, thereby to obtain the cosmetic product, the pharmaceutical product, the cable-filling product or the filled cable product.

According to a fifth aspect of the invention, there is provided a process for preparing the petrolatum composition of the first aspect of the invention, the process comprising:

mixing a wax having an average number of carbon atoms per molecule of between 25 and 70, and having between 5 and 50 wt % branched paraffins in which the branches are selected from methyl and ethyl branches, with a linear paraffin having an average number of carbon atoms per molecule of between 10 and 20, and optionally, a low melt wax, thereby to obtain the petrolatum composition, with sufficient of the wax and the linear paraffin being used such that the petrolatum composition has from 10 to 60 wt % of the wax and from 10 to 60 wt % of the linear paraffin, and with the petrolatum composition having a drop melt point of from 35° C. to 80° C.

The process may include adding from 10 to 60 wt % of the low melt wax having an average number of carbon atoms per molecule of between 20 and 30.

According to a sixth aspect of the invention, there is provided a cosmetic composition comprising between 10 and 40 wt % of the petrolatum composition of the first aspect of the invention.

The invention will now be described in more detail with reference to the following non-limiting examples, and the accompanying drawings.

Figure 2:
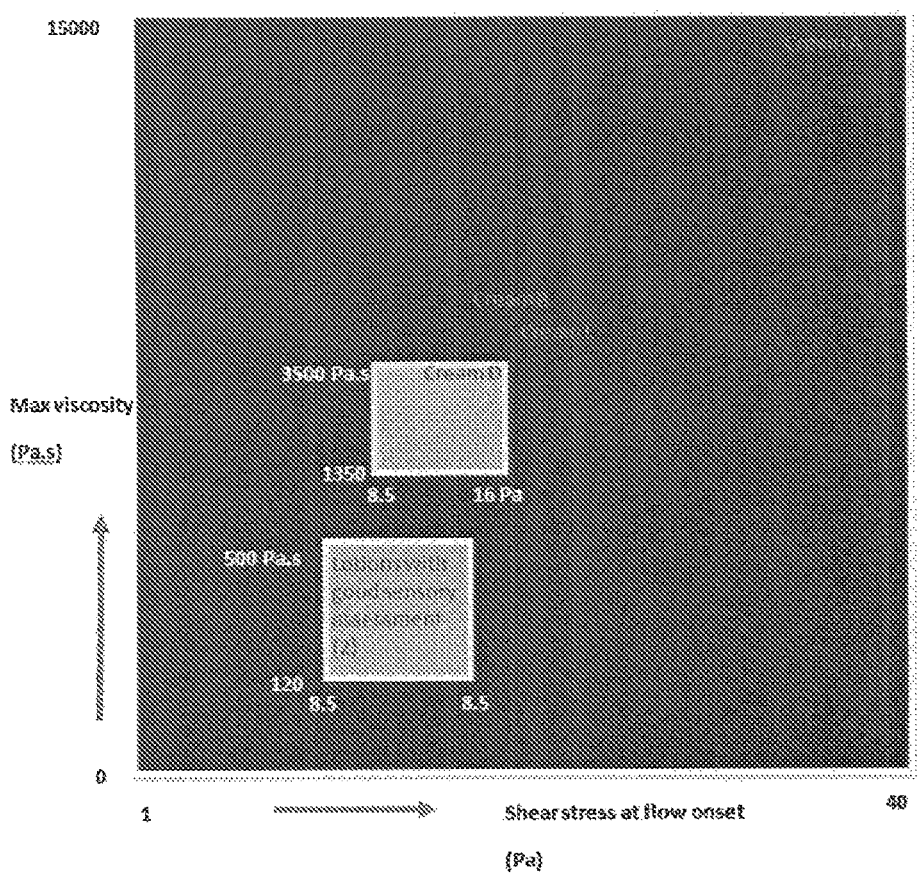

In the drawings,

FIG. 1 shows, for Example 2, viscosity curves of O/W emulsions assessed as good (cream D) and less good (Creams A, B and C); and FIG. 2 shows, for Example 2, boundaries for the onset of flow and maximum viscosity in the region of good primary skin feeling for creams and lotions.

EXAMPLE 1

Production of Petrolatums

Petrolatum compositions/samples were produced by the following preparation method: In each case, the wax component and the low melt wax component were melted in an oven at 100° C. The paraffin that is liquid at room temperature was also pre-heated in an oven at 100° C. The molten waxes were transferred to a clean stainless steel beaker and placed on a measuring scale in order to weigh out the amounts of wax required accurately according to the petroleum jelly formula. The temperature of the waxes was ascertained to be 80° C. before the liquid paraffin (also at 80° C.) was blended with the molten waxes. The solutions were stirred until the resultant blend was observed to be clear and thereafter left for 5 hours to congeal.

The components used had the properties described in Table 1 below. Viscosity was measured using the ASTM method D445. The drop melting point was measured using ASTM method D127.

TABLE 1

Description of petrolatum components

| Component | Description | Branching degree *** Mass % | Branching type | Drop Melting Point Unit °C. | Average carbon number **** | Viscosity cP |
|---|---|---|---|---|---|---|
| Wax Component | | | | | | |
| Sasolwax H1 | Hard *FT wax | 6 | Methyl | 110 | C41 | 8.0 @ 135° C. |
| Sasolwax HX35 | Hydro-isomerised hard *FT wax | 20 | Methyl | 108 | C40 | 9.0 @ 135° C. |
| Sasolwax C80M | Hard *FT wax | 10 | Methyl | 89 | C38 | 6.0 @ 100° C. |
| C30+ | A-olefin | 19 | Methyl | 70 | C30 | 6.4 @ 100° C. |
| C24-C28 a-olefin | A-olefin | 10 | Methyl | 52 | C26 | 2.3 @ 100° C. |
| Low Melt Wax | | | | | | |
| Sasolwax F5 | Medium *FT wax | 12 | Methyl | 50 | C27 | 3.6 @ 100° C. |
| Sasolwax Waksol A | Semi-liquid *FT wax | 13 | Methyl | 28 | C21 | 5.6 @ 40° C. |
| Linear Paraffin | | | | | | |
| Sasolwax C14-C20 paraffin | Liquid paraffin | 8 | Methyl | — | C17 | 2.9 @ 40° C. |
| Sasolwax C9-C11 paraffin | Liquid paraffin | 8 | Methyl | — | C10 | 2.6 @ 40° C. |
| Crude oil based feedstock: | | | | | | |
| Sasolwax 7836 | Microwax | 82 | C > 1 chains | 73 | C55 | 12.8 @ 100° C. |
| Slack wax | Medium wax | 39 | C > 1 chains | 40 | C28 | 3.7 @ 100° C. |
| Mineral oil | Liquid oil | 29 | **C > 1 chains | — | C23 | 12.5 @ 40° C. |

*FT Fischer Tropsch
**also contains 63% cyclic components
***Molecules having at least one branch on the carbon backbone, as a percentage of all molecules (in mass %)
****Average number of carbon atoms per molecule Determining of Branching Type and Degree of Components The branching type and degree of each of the components of the petrolatum composition was determined by High-Temperature GC (HTGC) using a Varian CP-3800 GC. $H_2$ was used as carrier gas. A Restek MXT-1 capillary column (100% crosslinked dimethyl-polysiloxane) was used (length: 15 m, internal diameter: 0.28 mm, phase thickness: 0.15 μm). Injection was by means of a programmable on-column injector, and a flame ionization detector (FID) was used. Xylene was used as a solvent for the wax. Table 2 shows the conditions employed in this method.

TABLE 2

GC Method used for the analyses of the wax samples

| Injector | |
|---|---|
| Initial Temperature (° C.): | 40 |
| Initial Holding Time (mins): | 0 |
| Ramp Rate (° C./min): | 70 |
| Temperature (° C.): | 420 |
| Holding Time (mins): | 49.57 |
| Total Time (mins): | 55 |
| EFC Flow Program | |
| Flow (ml/min): | 3.5 |
| Holding Time (mins): | 55.0 |

TABLE 2-continued

GC Method used for the analyses of the wax samples

| Column | |
|---|---|
| Initial Temperature (° C.): | 40 |
| Initial Holding Time (mins): | 5 |
| Ramp Rate (° C./min): | 10 |
| Final Temperature (° C.): | 440 |
| Final Holding Time (mins): | 10 |
| Total Time (mins): | 55 |
| Detector (FID) | |
| $N_2$ make-up flow (ml/min): | 25 |
| $H_2$ flow (ml/min): | 30 |
| Air flow (ml/min): | 300 |
| Detector Temperature (° C.): | 450 |

Properties of Petrolatum Compositions/Samples

The formulations and property analyses results are shown in Table 3 below.

TABLE 3

Petroleum jelly formulations and properties

| Raw material | Sample 1 ◊◊◊ | 2 | 3 | 4 | 5 | 6 | 7 |
|---|---|---|---|---|---|---|---|
| Sasolwax 7836 ◊ | 30 | — | — | — | — | — | — |
| Slack wax ◊ | 20 | — | — | — | — | — | — |
| Mineral oil ◊ | 45 | — | — | — | — | — | — |
| Wax Component | | | | | | | |
| Sasolwax H1 | — | — | 20 | — | — | — | — |
| Sasolwax HX35 | — | 20 | — | 20 | 20 | 30 | 4 |
| Sasolwax C80M | — | 5 | 5 | 5 | — | — | 6 |
| C30+ | — | 5 | 5 | 5 | 10 | — | — |
| C24-C28 a-olefin | — | — | — | — | — | — | 19 |
| Low Melt Wax | | | | | | | |
| Sasolwax F5 | 5 | 5 | 5 | 5 | 10 | 20 | 4 |
| Sasolwax Waksol A | — | 35 | 35 | 35 | 30 | 20 | 35 |
| Linear Paraffin | | | | | | | |
| Sasolwax C14-C20 paraffin | — | 30 | 30 | — | 30 | 30 | 32 |
| Sasolwax C9-C11 paraffin | — | — | — | 30 | — | — | — |
| Total crude oil derived (◊) content (%): | 95 | 0 | 0 | 0 | 0 | 0 | 0 |
| Total Synthetic content (%): | 5 | 100 | 100 | 100 | 100 | 100 | 100 |
| Appearance | White, unctuous paste ◊◊ | White, unctuous paste | White, unctuous paste | Hard wax-like product Not a petrolatum | White, unctuous paste | White, unctuous paste | White, unctuous paste | White, unctuous paste |
| Drop melting point (° C.) | 35-70 ◊◊ | 60.4 | 69.8 | 72.5 | 65.5 | 65.1 | 63.5 | 69.5 |
| Cone penetration (0.1 mm) | 60-300 ◊◊ | 160 | 162 | 20 | 170 | 185 | 187 | 167 |

◊◊ Eur. Pharm requirement
◊◊◊ Comparative example

All samples shown in Table 3 pass polycyclic aromatic hydrocarbon, identification, acidity/alkalinity and sulphated ash testing as prescribed by the Eur. Pharm.

EXAMPLE 2

Use of Petrolatums in Personal Care Products
General Experimental Conditions

Rheology is the science of deformation and flow of substances as a function of the shear rate or shear stress applied to the product. The rheological measurements for this Example were conducted using an Anton Paar rheometer (Anton Paar GmbH, Osterreich, Austria). The Anton Paar rheometer is a strain-controlled rheometer that is capable of both dynamic or steady shear strain measurements and measuring the resultant torque values exerted by the sample in response to the imposed shear strain. The dynamic/steady shear strain is applied by the step-motor and the torque is measured by the force rebalance transducer (FRT).

T. K. Parkins, J. B. Turner, Starting Behavior of Gathering Lines and Pipelines Filled with Gelled Prudhoe Bay J. Pet. Technol. 23 (1971) 301-308 found that the thermal and shear history, aging and composition of a jelly significantly affect the yield stress measurement. In all measurements carried out in this Example, a freshly prepared sample was used and the sample was rested for 40 min after loading to allow material relaxation and temperature equilibration. It was found that 40 min is enough time to allow the samples to be completely relaxed and to be thermally equilibrated. All measurements were repeated at least three times for each test and highly reproducible data were obtained within the coefficient of variation of ±5% in all cases.

In this Example, all measurements were performed with a parallel-plate fixture with a radius of 25 mm and a gap size of 2.5 mm. The larger gap size between the two plates ensures smaller gap error.

Measurement Methods for the Study of Primary Skin Feeling

During this investigation the onset of flow $\tau_F$ of cream samples was determined from the maximum of the viscosity curve $\eta_{max}$ (FIG. 1).

Sensory assessment results were obtained from a panel comprising of 15 people of different age groups, sex and ethnicity. The panel was asked to assess and rate four cream samples, a value of 10 being a product with good sensory assessment and a value of 0 being a product with poor sensory assessment (Table 4). The samples were assessed during a blind test and the samples that the panel received were labelled Creams A-D.

TABLE 4

Panel sensory assessment and rheological measurement results

| Product | % Fischer-Tropsch wax in Petroleum Jelly used in Cream | Shear stress (flow onset) $T_F$ (Pa) | Dynamic maximum viscosity $\eta_{max}$ (Pa · s) | Sensory assessment* |
|---|---|---|---|---|
| Cream A | 0 | 36 | 14700 | 5 |
| Cream B | 0 | 21 | 6700 | 6 |
| Cream C | 100** | 26 | 4680 | 7 |
| Cream D | 65 | 16 | 3400 | 8 |

*10, very good . . . 1, poor
**Petrolatum composition of Sample 2, in Table 3, above.

Creams A-D are all products based on the following formulation (Table 5).

TABLE 5

Cream formulation tested

| Ingredient | % | Function |
|---|---|---|
| Aqua | 66.3 | Vehicle |
| Disodium EDTA | 0.1 | Chelating |
| Propylene Glycol | 1.5 | Humectant |
| Glycerine | 3.5 | Humectant |
| Lipowax R2 | 6 | Viscosity modifier/Stabiliser |
| Lipomulse 165 | 2.5 | Emulsifier |
| Mineral Oil | 4 | Emolient |
| Petrolatum | 15 | Oclusive/Emolient |
| Microcare DMP | 0.6 | Preservative |
| Parfum | 0.5 | Fragrance |

The cream formulation used contains 15% petroleum jelly or petrolatum (Table 5), and a range of between 0-100% Fischer Tropsch petroleum jelly products were used to prepare emulsions (Table 4). Cream A contained 0% Fischer-Tropsch wax and is a traditional mineral based petroleum jelly. Cream B also contains a 100% mineral based petroleum jelly with a slightly different formulation than the petroleum jelly used in Cream A. Cream C contains a petroleum jelly that is fully based on Fischer-Tropsch wax; whereas for Cream D a predominantly synthetic petroleum jelly containing 65% Fischer-Tropsch wax was used.

The sensory assessment for spreadability of the product by the panel was correlated with the maximum viscosity and shear stress measured at the onset of flow, being depicted by the window as shown in FIG. 2. The boundaries of the window were determined by the results of cream samples obtaining good sensory assessment results by a panel of people as shown in FIG. 2. The graphical window is depicted as measured values for the shear stress and maximum viscosity at the onset of flow, providing the upper and lower limit for products with good sensory assessment. FIG. 2 shows where products in accordance with the invention feature in relation to rheological properties measured compared to literature data of creams with good skin feeling assessment.

As shown in FIG. 2 only Cream D (containing 65% Fischer-Tropsch wax) tested during this investigation falls within this window of good primary skin feel as found by R. Brummer, S. Gorderskty, Rheological studies to objectify sensations occurring when cosmetic emulsions are applied to the skin, Colloids and Surfaces, Physicochemical and Engineering Aspects 152 (1999) 89-94. During this investigation it was found that a formulation containing petroleum jelly based on 65% Fischer-Tropsch wax raw material has the best primary sensory assessment or spreadability when compared to traditional mineral based products. Comments from the panel regarding Cream D were that it had a smooth application and was easily absorbed. The 100% Fischer-Tropsch based petroleum jelly Cream C falls just outside the boundary for good sensory assessment. Cream C is closer to the window than the mineral based products, Cream A and B. Cream C was also given a higher rating by the panel. It is interesting to note that the further away a product falls from the window defined for good sensory assessment (2); the lower the rating that was given by the panel. Cream A is the furthest away from the window and was also given the lowest rating by the panel.

The invention claimed is:

1. A petrolatum composition comprising
    from 10 to 60 wt % of a wax having an average number of carbon atoms per molecule of between 25 and 70, and having between 10 and 50 wt % branched paraffins in which the branches are selected from methyl and ethyl branches;
    from 10 to 60 wt % of a linear paraffin having an average number of carbon atoms per molecule of between 10 and 20; and
    optionally, a low melt wax;
    with the petrolatum composition having a drop melt point of from 35° C. to 70° C. and a cone penetration (as measured by ASTM D937-07, employing the cone defined in ASTM D217-10) of between 60 and 300 mm/10.

2. The petrolatum composition according to claim 1, wherein the wax is a synthetic wax.

3. The petrolatum composition according to claim 1, wherein the wax makes up from 20 to 40 wt % of the petrolatum composition.

4. The petrolatum composition according to claim 1, wherein the wax is selected from the group consisting of a hydroisomerized wax, a hydroisomerized Fischer-Tropsch wax, an alpha-olefin wax and a Fischer-Tropsch wax.

5. The petrolatum composition according to claim 1, wherein the linear paraffin is a Fischer-Tropsch derived paraffin.

6. The petrolatum composition according to claim 1, wherein the linear paraffin makes up from 20 to 40 wt % of the petrolatum composition.

7. The petrolatum composition according to claim 1, which includes the low melt wax and wherein the low melt wax has an average number of carbon atoms per molecule of between 20 and 30.

8. The petrolatum composition according to claim 7 wherein the low melt wax is a Fischer-Tropsch wax.

9. The petrolatum composition according to claim 1, wherein each of the wax component and the linear paraffin component are synthetic.

10. The petrolatum composition according to claim 9, wherein the low melt wax is present, and is a synthetic wax.

11. A method of making a cosmetic product, a pharmaceutical product, a cable-filling product or a filled cable product which includes adding the petrolatum composition according to claim 1, to a cosmetic composition or substance, to a pharmaceutical composition or substance, to a cable-filling composition or substance, or to a cable or cable component, thereby to obtain the cosmetic product, the pharmaceutical product, the cable-filling product or the filled cable product.

12. A process for preparing the petrolatum composition of claim 1, the process comprising:
    mixing a wax having an average number of carbon atoms per molecule of between 25 and 70, and having between 10 and 50 wt % branched paraffins in which the branches are selected from methyl and ethyl branches, with a linear paraffin having an average number of carbon atoms per molecule of between 10 and 20, and optionally, a low melt wax, thereby to obtain the petrolatum composition, with sufficient of the wax and the linear paraffin being used such that the petrolatum composition has from 10 to 60 wt % of the wax and from 10 to 60 wt % of the linear paraffin, and with the petrolatum composition having a drop melt point of from 35° C. to 70° C. and a cone penetration (as measured by ASTM D937-07, employing the cone defined in ASTM D217-10) of between 60 and 300 mm/10.

13. A cosmetic composition comprising between 10 and 40 wt % of the petrolatum composition of claim 1.

14. A petrolatum composition comprising from 10 to 60 wt % of a wax having an average number of carbon atoms per molecule of between 25 and 70, and having between 10 and 50 wt % branched paraffins in which the branches are selected from methyl and ethyl branches;

from 10 to 60 wt % of a linear paraffin having an average number of carbon atoms per molecule of between 10 and 20; and a low melt wax;

with the petrolatum composition having a drop melt point of from 35° C. to 70° C. and a cone penetration (as measured by ASTM D937-07, employing the cone defined in ASTM D217-10) of between 60 and 300mm/10.

\* \* \* \* \*